United States Patent [19]

Gaetani et al.

[11] Patent Number: 5,360,804
[45] Date of Patent: Nov. 1, 1994

[54] MULTICOMPONENT AGENT OR KIT FOR PREPARING THE SULPHO-CONJUGATED FORM OF PYRIDINO, PYRIMIDINO OR TRIAZINO N-OXIDE COMPOUNDS AND METHOD OF USE

[75] Inventors: Quintino Gaetani, Sevran; André Rougier, Le Raincy; Albert Duranton; Michel Hocquaux, both of Paris, all of France

[73] Assignee: L'Oreal, Paris, France

[21] Appl. No.: 805,943

[22] Filed: Dec. 12, 1991

[30] Foreign Application Priority Data

Dec. 28, 1990 [FR] France .................................. 90 16504

[51] Int. Cl.$^5$ .................. A61K 31/53; A61K 31/505; A61K 31/44
[52] U.S. Cl. .................................... 514/245; 514/212; 514/235.5; 514/235.8; 514/244; 514/269; 514/272; 514/275; 514/318; 514/340; 514/360; 540/597; 540/598; 540/601; 544/113; 544/122; 544/124; 544/196; 544/204; 544/213; 544/219; 544/319; 544/320; 544/321; 544/323; 544/326; 544/330; 544/333; 546/193; 546/290; 546/297; 546/307
[58] Field of Search ................... 514/212, 235.5, 235.8, 514/241, 245, 269, 272, 275, 318, 360, 340; 540/597, 598, 601; 544/113, 122, 124, 196, 204, 213, 219, 319, 320, 321, 323, 321, 330, 333; 546/193, 290, 297, 307

[56] References Cited

U.S. PATENT DOCUMENTS

| | | | |
|---|---|---|---|
| 3,270,014 | 8/1966 | Ursprung et al. | 260/247.5 |
| 3,270,015 | 8/1966 | Ursprung et al. | 260/247.5 |
| 3,270,018 | 8/1966 | Ursprung et al. | 260/249.9 |
| 3,475,340 | 10/1969 | Bollock | 252/301.1 |
| 3,910,928 | 10/1975 | McCall et al. | 260/293.51 |
| 4,032,559 | 6/1977 | McCall et al. | 260/265.5 R |
| 4,287,338 | 9/1981 | McCall | 544/123 |

FOREIGN PATENT DOCUMENTS

| | | |
|---|---|---|
| 0356271 | 2/1990 | European Pat. Off. . |
| 2651122 | 8/1989 | France . |
| 2657609 | 1/1990 | France . |
| 2662607 | 5/1990 | France . |
| 2663327 | 6/1990 | France . |
| 2071092 | 3/1981 | United Kingdom . |
| WO86/04231 | 7/1986 | WIPO . |

OTHER PUBLICATIONS

McCall, J. et al., "Pyrimidine and Triazine 3-Oxide Sulfates: A New Family of Vasodilators", J. Med. Chem., 1983, 26, pp. 1791-1793.
Patent Abstracts of Japan, vol. 11, No. 398 (C–466) (2845) 25 Dec. 1987 (JP-A-62 158204, 14 Jul. 1987).
Gilbert, E., "The Reactions of Sulfur Trioxide, and of Its Adducts, With Organic Compounds", Chem. Rev., (1969), 62, 549-589.

*Primary Examiner*—Robert T. Bond
*Assistant Examiner*—Y. N. Gupta
*Attorney, Agent, or Firm*—Jacobson, Price, Holman & Stern

[57] ABSTRACT

Multicomponent agent or kit for preparing the sulpho-conjugated form of pyridino, pyrimidino or triazino N-oxide compounds and method of use.

The present invention relates to a multicomponent agent or kit for preparing the sulpho-conjugated form of pyridino, pyrimidino or triazino N-oxide compounds, comprising at least one compound of the pyridino, pyrimidino or triazino N-oxide type, on the one hand, and a sulphating agent, on the other hand.

13 Claims, No Drawings

MULTICOMPONENT AGENT OR KIT FOR PREPARING THE SULPHO-CONJUGATED FORM OF PYRIDINO, PYRIMIDINO OR TRIAZINO N-OXIDE COMPOUNDS AND METHOD OF USE

The present invention relates to a multicomponent agent or kit for preparing the sulpho-conjugated form of pyridino, pyrimidino or triazino N-oxide compounds as well as a method for its use.

Some sulphate derivatives of pyridines, pyrimidines and triazines have been described in U.S. Pat. No. 4,287,338, in particular for the systemic treatment of hypertension. The topical application of the internal sulphate salts of pyrimidines to the stimulation of hair regrowth is a subject of Patent Application WO 86-04231. This document describes in particular the use of the inner salt of the hydroxide of 2,4-diamino-6-piperidinyl-3-sulphoxypyrimidinium, also known by the name "minoxidil sulphate".

This compound has the disadvantage of being difficult to obtain by synthesis and of being unstable on storage in an aqueous or aqueous-alcoholic medium. In order to guarantee its good preservation and to prevent its decomposition, it is necessary to store it at $-15°$ C. Moreover, it has proved difficult to prepare, isolate and purify a sulphate which is chemically pure, on the one hand, and, on the other hand, a solution of "minoxidil sulphate" in an aqueous medium has a ½-life of 48 hours. As a result, the product cannot be applied on an industrial scale and, because of half-lives of this order of magnitude, this compound, prepared by synthesis, is poorly compatible, in particular with therapeutic uses.

Other compounds of the pyridino, pyrimidino or triazino N-oxide type in the sulpho-conjugated form exhibit the same disadvantages and may have an even shorter half-life.

The present invention relates to multicomponent agents or "kits" for preparing the sulpho-conjugated form of pyridino, pyrimidino, or triazino N-oxide compounds intended to be brought into contact before use, characterised in that they comprise at least:

a) a component comprising at least one compound of formula (I):

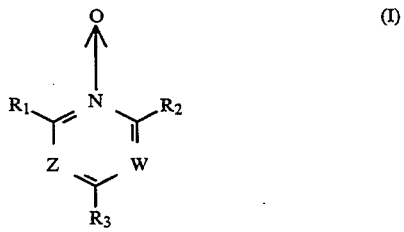

in which:

$R^1$ and $R^2$ denote a $C_1$ to $C_8$ lower alkyl or an amino group;

W and Z each denote a —CH= or —N= group;

$R^3$ denotes a

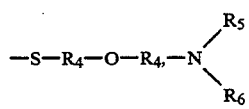

or —H group; and $R^4$ denotes a linear or branched $C_1$ to $C_{18}$ alkyl group which is unsubstituted or substituted by one or more halogen atoms, a $C_1$ to $C_{18}$ alkenyl, $C_3$ to $C_7$ cycloalkyl, aryl or aralkyl group;

$R^5$ and $R^6$ denote, independently of each other, a hydrogen atom or a group such as defined for $R^4$; or $R^5$ and $R^6$ form with the nitrogen to which they are attached, a heterocyclic residue chosen from the group consisting of piperidino, pyrrolidinyl, morpholino, 2,4,4-trimethylazetidinyl, 2,3,4-trimethylazetidinyl, 2-methylpyrrolidinyl, 3-butylpyrrolidinyl, 2-isohexylpyrrolidinyl, 2,3-dimethylpyrrolidinyl, 2,2-dimethylpyrrolidinyl, 2,5-diethylpyrrolidinyl, 3-tert-butylpyrrolidinyl, 2,3,5-trimethylpyrrolidinyl, 3,4-dioctylpyrrolidinyl , 2-methylpiperidino, 3-methylpiperidino, 4-methylpiperidino, 3-isopropylpiperidino, 4-tert-butylpiperidino, 2-methyl-5-ethylpiperidino, 3,5-dipentylpiperidino, 2,4,6-trimethylpiperidino, 2,6-dimethylpiperidino, 2,6-dimethyl-4-octylpiperidino, 2,3,5-trimethylpiperidino, 2-ethylhexahydroazepinyl, 4-tert-butylhexahydroazepinyl, 3-heptylhexahydroazepinyl, 2,4-dimethylhexahydroazepinyl, 3,3-dimethylhexahydroazepinyl, 2,4,6-tripropylhexahydroazepinyl, 2-methylheptamethyleneimino, 5-butylheptamethylene-imino, 2,4-diisopropylheptamethyleneimino, 3,3-diethylheptamethylene-imino, 2,5,8-trimethylheptamethylene-imino, 3-methyloctamethyleneimino, 2,9-diethyloctamethylene-imino, 4-isooctyloctamethylene-imino, 2-ethylmorpholino, 2-methyl-5-ethylmorpholino, 3,3-dimethylmorpholino, 2,6-di-tert-butylmorpholino, 4-methylpiperazinyl, 4-isopropylpiperazinyl, 2-methylaziridinyl, 2-ethylaziridinyl, 2-butylaziridinyl, 2,3-dimethylaziridinyl, 2,2-dimethylaziridinyl, 2-methylazetidinyl, 3-methylazetidinyl, 2-octylazetidinyl, 2,2-dimethylazetidinyl and 3,3-diethylazetidinyl groups; or their addition salts with acids; and b) a component comprising at least one sulphating agent.

The components a) and b) may be in solid form, the agent or "kit" in that case comprising a third component c) consisting of a liquid medium, a vehicle which is capable of dissolving the components a) and b) and of forming with the components a) and b), at the end of the reaction, a physiologically acceptable medium.

The component c) is intended to be added to the component a) or b) before being brought into contact with b) or a), respectively, or to the components a) and b) after they have been brought into contact.

The present invention therefore solves the problems of the difficulty of synthesis and stability of the sulpho-conjugated forms which can thus be prepared immediately before their use and, as will emerge from the examples, can retain a prolonged activity such that after their preparation, they may be used for one week with daily application.

The compound of formula (I) is brought into contact with an $SO_3$ generator in a reaction medium.

The reaction medium results either from the mixing of a) and b), or from the mixing of a) and c) and then b), from the mixing of b) and c) and then a) or from the mixing of a) and b) and then c).

Application or administration may be carried out for the purpose of treating hypertension, alopecia or desquamative dermatitis or for cosmetic treatment purposes.

The pyridine derivatives of formula (I) may be prepared in particular according to the methods described in U.S. Pat. Nos. 3,910,928, 4,032,559, EP-A-356,271, FR-89/11352, FR-90/01148 or FR-90/06693

The pyrimidine derivatives of formula (I) may be prepared in particular according to the methods described in U.S. Pat. Nos. 3,910,928, 4,032,559, EP-A-356,271, FR-89/11352, FR-90/01148 or FR-90/06693.

The triazine derivatives may be prepared in particular according to the methods described in U.S. Pat. Nos. 3,475,340, 3,270,014, 3,270,018, 3,270,015 or FR-90/07664.

As suitable acids for the addition salts with acids of the compounds of formula (I), there may be mentioned in particular hydrochloric, hydrobromic, sulphuric, phosphoric, nitric, acetic, benzoic, salicylic, glycolic, succinic, nicotinic, tartaric, maleic, malic, palmoic, methanesulphonic, cyclohexanesulphamic, picric, lactic and aceturic acids in particular.

In the formula (I), lower alkyl represents $C_1$ to $C_8$ alkyls and in particular methyl, ethyl, n-propyl, isopropyl, n-butyl, isobutyl, 2-methylpropyl, n-pentyl, n-hexyl, n-heptyl or n-octyl radicals.

The $C_1$ to $C_{18}$ alkyl radicals are chosen more particularly from n-dodecyl, n-octyl, n-hexyl, n-butyl and ethyl.

The alkenyl radicals denote more particularly allyl, 1-methylallyl, 2-methylallyl or methallyl, 2-butenyl (crotyl), 3-butenyl, 1,2-dimethylallyl, 1,1-dimethylallyl, 2-ethylallyl, 1-methyl-2-butenyl, 2-methyl-2-butenyl, 2-methyl-2-butenyl, 3-pentenyl, 2,3-dimethyl-2-butenyl, 1,1,2-trimethylallyl, 1,3-dimethyl-2-butenyl, 1-ethyl-2-butenyl, 4-methyl-2-pentenyl, 2-ethyl-2-pentenyl, 4,4-dimethyl-2-pentenyl, 2-heptenyl, 2-octenyl, 5-octenyl, 1,4-dimethyl-4-hexenyl.

Cycloalkyl denotes more particularly cyctopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl or cyclooctyl.

Aryl designates more particularly phenyl, 2,4-dimethylphenyl, 2,6-dimethoxyphenyl or 2,4-dichlorophenyl.

Aralkyl is understood as meaning more particularly benzyl, phenetyl, 1-phenylethyl, 2-phenylpropyl, 4-phenylbutyl, 5-phenyl-2-methylpentyl, 1-naphthylmethyl, 2-(1-naphthyl)ethyl or 2-(2-naphthyl)ethyl.

Amongst the compounds of formula (I) there may be mentioned minoxidil, 2,4-diamino-6-piperidinotriazine 3-oxide, 2-amino-4-methyl-6-piperidinopyrimidine 3-oxide, 2-methyl-4-amino-6-piperidinopyrimidine 3-oxide, 2,4-dimethyl-6-piperidinopyrimidine3-oxide, 2,4-diamino-6-n-butyloxypyrimidine 3-oxide, 2,4-diamino-6-(n-hexylamino)pyrimidine 3-oxide and 2,6-diamino-4-piperidinopyridine 1-oxide.

Sulphating agent as used in component b) according to the invention is understood as meaning $SO_3$ generators such as described in the article by E. GILBERT, Chem. Rev. (1962), 62, 549–589, chosen for example from $SO_3$ and tertiary amine complexes and more particularly $SO_3$ and mono- or polyfunctional amine complexes, including the amines located on the side groups of polymer chains. According to the invention, the $SO_3$-trimethylamine and $SO_3$-triethylamine complexes are preferably used.

The agents or "kits" according to the invention are intended to convert the compounds of formula (I) into their sulpho-conjugated form of formula (II) in accordance with the scheme below:

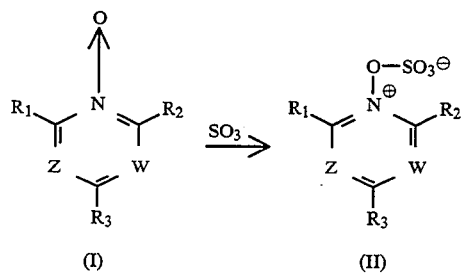

where the substituents $R^1$, $R^2$, $R^3$, Z and W have the meanings given above, in a physiologically acceptable medium.

Once the sulphation reaction is completed, the sulpho-conjugated form may be directly used, in the reaction medium, in a therapeutic or cosmetic treatment. Thus, the reaction medium may serve as the application vehicle.

In order to obtain a reaction medium which is also the application vehicle, the device according to the invention may be provided in the form of a two compartment container. In this embodiment, the first compartment contains the first component, preferably in the form of a solution and the second compartment contains the second component in liquid or solid form, the contents of the two compartments being intended to be mixed before use in order to form a physiologically acceptable medium.

The physiologically acceptable media may be aqueous, aqueous-alcoholic or anhydrous.

For preparations for therapeutic use to be taken by mouth, aqueous media or media having a low alcohol content are particularly preferred and for preparations for therapeutic or cosmetic use by topical application, aqueous-alcoholic, alcoholic or anhydrous media may be provided.

For the preparations for topical use, the medium may also contain other excipients such as propylene glycol, glycol or polyol ethers, thickening agents, stabilisers and surfactants in particular.

Irrespective of whether the preparation comprising a sulpho-conjugated form is intended for oral or topical application, the pH of the preparation is about 7 and preferably between 5 and 9.

According to the invention, the concentrations of N-oxide compounds used depend on the activity of the compound, its safety and also its mode of administration. The concentration of the sulpho-conjugated form of formula (II) is between 0.1 and 10% by weight of the mixture of all the components.

As for the amount of sulphating agents, this depends on the activity of the agent and the kinetics of the reaction and also on the level of sulphation desired in the preparation. In the case where a fast rate or a high level of sulphation is required, an excess of sulphating agent will preferably be used, it being possible for the amount of sulphating agent contained in the component b) to be as high as 100 molar equivalents of the amount of N- oxide compound of formula (I) contained in the component a).

The reaction time of the compounds of formula (I) with the SO₃-amine complex may range from about 5 minutes to about 2 hours.

According to the invention, a specific embodiment consists of an agent or kit comprising two components. The first component (a) is provided in the form of a solution of the compound of formula (I) in an alcoholic, aqueous-alcoholic or aqueous mixture.

A second component (b) is provided in solid form, for example in the form of a compressed pellet containing the sulphating agent and an acceptable solid vehicle.

The second component (b) may in particular be provided in the form of an effervescent tablet comprising the sulphating agent and a carbon dioxide gas generating system capable of producing the effervescence, this system being composed of an acid chosen from water-soluble solid acids such as aliphatic acids such as acetic, propionic, butyric and valetic acids; dicarboxylic acids such as oxalic, malonic, succinic, glutaric, adipic, pimelic, fumaric, maleic, phthalic, isophthalic and terephthalic acid; amino acids such as glutamic acid; hydroxy acids such as lactic, malic, tartaric and citric acid, as well as their salts.

The acids may also be chosen from inorganic acids such as phosphoric acid and its salts such as the acid salts of potassium or sodium or alternatively the sulphites or bisulphites of sodium or potassium or ammonium.

The second constituent of the effervescent system is a carbonate such as a sodium, potassium or ammonium carbonate or bicarbonate.

The weight ratio of the acid to the carbonate is such as to produce the effervescence, and may vary depending on the nature of the acid and the carbonate. Generally, the carbonate is present in proportions of 5 to 80% by weight of the effervescent system and the acid in proportions of 20 to 85%.

The amount of effervescent system relative to the weight of the tablet being preferably between 50 and 80% by weight.

Before use, the component b) is mixed with the component a) in the form of a solution. After a suitable reaction time, the compound of initial formula (I) is totally or partially present in sulpho-conjugated form. The reaction product may then be directly applied to the topical application zones or may be ingested.

It is possible to improve the reaction kinetics of the present method by supplying heat. This supply may be provided-externally or alternatively generated by exothermic reaction of adjuvants.

The sulpho-conjugated derivatives thus prepared may exhibit, in the same medium, an improved stability relative to the "sulphates" prepared by synthesis.

The present invention also relates to a method for using the agents according to the invention, characterised in that the components a), b) and, optionally, c), defined above, are brought into contact in one of the following orders:
a) is brought into contact with b)
a) is mixed with c) and the resulting mixture a)+c) is brought into contact with b)
b) is mixed with c) and the resulting mixture b)+c) is brought into contact with a)
a) is brought into contact with b), the resulting product being mixed with c).

The present invention also relates to the method for preparing the ready-to-use, sulpho-conjugated form of pyridino, pyrimidino or triazino N-oxide compounds, characterised in that:
a/ a component is stored which comprises at least one compound of formula (I):

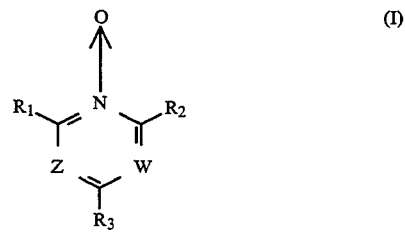

in which the substituents are defined above,
b/ a component is stored which comprises at least one sulphating agent, and
c/ the stored components are mixed.

The invention also relates to the use of the multicomponent agents or "kits" according to the invention, for preparing the sulpho-conjugated form of pyridino, pyrimidino or triazino N-oxide compounds intended for the treatment of hypertension as well as to the use of the device for preparing this sulpho-conjugated forth intended for the treatment of hair loss or for stimulating its regrowth.

The following examples are intended to describe the invention without limiting its scope.

EXAMPLE 1

60 mg of powdered SO₃-N,N-diisopropylethylamine complex packaged under an inert atmosphere are introduced into a single dose bottle containing 2 ml of a 50° alcoholic solution of 1% minoxidil and 100 mg of sodium bicarbonate. After a few minutes of gas evolution, the solution acquires an orange colour and the pH is stabilised at 7.

Five minutes after the start of mixing, thin-layer chromatography (TLC) on silica plates is carried out on the solution. After eluting with an ethyl acetate/methanol (80/20) mixture, only one spot corresponding to the minoxidil O-sulphate ($R_f$=0.88, $R_f$ minoxidil=0.15) is observed under UV at 254 nm.

EXAMPLE 2

3 ml of 1% minoxidil in a ternary ethanol/propylene glycol/water (50/20/30) mixture are packaged in a single dose bottle. 90 mg of powdered SO₃-triethylamine complex packaged under an inert atmosphere are added. After stirring gently and leaving in contact for 5 minutes, the mixture becomes homogeneous and the pH is stabilised at 8.

Deposited on a silica plate and after elution with an ethyl acetate/methanol (80/20) mixture, the solution reveals under UV, a large spot corresponding to minoxidil O-sulphate and a spot corresponding to residual minoxidil.

Allowed to stand at room temperature, the same solution after 50 minutes now shows in TLC only one spot corresponding to the sulphate.

EXAMPLE 3

2 ml of 1% minoxidil in a binary absolute ethanol/propylene glycol (95/5) mixture are packaged in a single dose bottle. 20 mg of powdered SO₃-triethylamine complex packaged under an inert atmosphere are added to this solution.

After mixing gently and leaving in contact for 10 minutes, the mixture became homogeneous. After TLC on silica plates and elution with an ethyl acetate/methanol (50/50) mixture, a very predominant spot corresponding to the sulphate ($R_f=0.9$) and a faint spot corresponding to the minoxidil ($R_f=0.3$) are observed under UV.

EXAMPLE 4

A mixture of 100 mg of sodium bicarbonate and 150 mg of $SO_3$-poly(4-vinylpyridine) complex containing 2.2 mmols $SO_3$/g are added to 2 ml of 1% minoxidil in an ethanol/water (50/50) mixture.

After a mild evolution of $CO_2$ and 15 minutes of contact, a slight deposit due to the insoluble polymeric vehicle is observed. The supernatant shows, in TLC on silica plates eluted with an ethyl acetate/methanol (50/50) mixture, a spot corresponding to minoxidil O-sulphate.

EXAMPLE 5

The following solid mixture prepared in a mortar:

| Citric acid (containing 1 H₂O) | 10 g |
| Sodium bicarbonate | 15 g |
| SO₃-trimethylamine complex | 5 g |

After grinding so as to produce a homogeneous powder, the mixture is packaged under an inert atmosphere in 0.3 g sachets.

A 0.5% solution of minoxidil in an aqueous-alcoholic mixture having an alcohol strength of 35° is separately packaged in single-dose bottles in an amount of 5 ml per bottle.

Before use, the contents of a sachet are added to a single-dose bottle. After the effervescence has ceased, after a few minutes, the solution has a pH of 6.

A level of sulphation of 50% is observed, by high performance liquid chromatographic assay of the minoxidil sulphate formed, after 30 minutes' contact at room temperature.

EXAMPLE 6

The following solid mixture is prepared in a mortar:

| Citric acid (containing 1 H₂O) | 10 g |
| Pure sodium bicarbonate | 15 g |
| SO₃-trimethylamine complex | 5 g |
| Silica gel 60 (230–400 mesh) | 20 g |

After grinding together until a fine homogeneous powder is obtained, the mixture is packaged under an inert atmosphere in 0.5 g sachets.

Separately, minoxidil is packaged in 5-ml units as in Example 5.

Before use, the contents of a sachet are added to a single-dose bottle of minoxidil. A foam-applicator tip is then fitted to the bottle.

During the effervescence, the tablet disintegrates and after a few minutes, only a slight deposit of silica remains at the bottom of the bottle, which will be retained by the foam-applicator tip.

A level of sulphation of the minoxidil of 50% is observed, by high performance liquid chromatographic assay, after 30 minutes' contact.

EXAMPLE 7

The following solid mixture is prepared in a mortar:

| Pure salicylic acid | 20 g |
| Sodium bicarbonate | 15 g |
| SO₃-trimethylamine complex | 5 g |
| Silica gel 60 (230-400 mesh) | 10 g |

After obtaining a homogeneous powder, 0.5 g tablets are prepared from this mixture and are packaged as troches in plasticised packs. Separately, the packaging of minoxidil in 5-ml single-dose bottles is carried out as in Example 5.

In order to obtain the sulphate preparation, an effervescent tablet is added to a single-dose bottle of minoxidil. During the effervescence, the tablet disintegrates and after a few minutes, only a slight deposit of silica remains at the bottom of the bottle, which will be retained by the foam-applicator tip.

After 30 minutes' contact, chromatographic assay shows a 50% level of sulphation. Allowing the preparation to stand at room temperature for several days results in a 42% level of sulphation after 7 days, with a pH of 7.5.

A composition prepared in this way therefore exhibits a greater stability relative to a composition prepared by dissolution of minoxidil sulphate, and may thus be suitable for a treatment lasting one week with daily application in the morning and in the evening.

EXAMPLE 8

The following ingredients are mixed in a mortar:

| Salicylic acid | 20 g |
| Potassium bicarbonate | 18 g |
| SO₃-trimethylamine complex | 10 g |
| Silica gel 60 (230–400 mesh) | 10 g |

After obtaining a homogeneous powder, 0.58-g tablets are prepared and are packaged as troches in protective packs.

Using a minoxidil packaging as in Example 5 and adding an effervescent tablet for a 5-ml dose of minoxidil, a 50% level of sulphation is obtained after 10 minutes. This level is maintained at 40% after allowing the preparation to stand for 7 days at room temperature.

EXAMPLE 9

An effervescent tablet prepared according to Example 8 is added to a single-dose bottle of 5 ml of a 0.5% solution in an aqueous-alcoholic mixture (containing 35% of alcohol) of 2,4-diamino-6-piperidinotriazine 3-oxide.

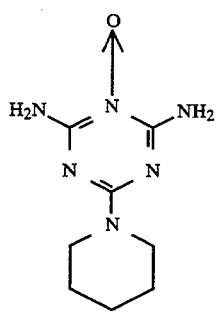

After the effervescence has ceased, the appearance of a sulpho-conjugated derivative spot is observed in TLC on silica plates after elution with an ethyl acetate/methanol (50/50) mixture.

| | |
|---|---|
| $R_f$ of the sulpho-conjugate | 0.93 |
| $R_f$ of the N-oxide | 0.35 |

EXAMPLE 10

The procedure is in every respect as in Example 9 using as N-oxide, the 2-amino-4-methyl-6-piperidinopyrimdine 3-oxide derivative.

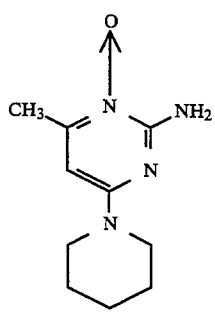

| | |
|---|---|
| $R_f$ of the sulpho-conjugate | 0.90 |
| $R_f$ of the N-oxide | 0.38 |

EXAMPLE 11

The procedure is as in Example 9 using as N-oxide, the 2-methyl-4-amino-6-piperidinopyrimidine 3-oxide derivative.

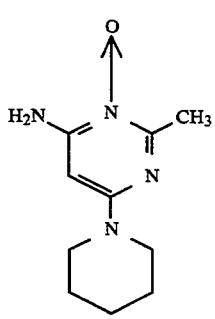

| | |
|---|---|
| $R_f$ of the sulpho-conjugate | 0.91 |
| $R_f$ of the N-oxide | 0.41 |

EXAMPLE 12

The procedure is as in Example 9 with the 2,4-dimethyl-6-piperidinopyrimidine 3-oxide derivative.

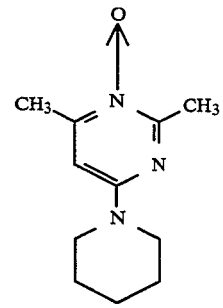

| | |
|---|---|
| $R_f$ of the sulpho-conjugate | 0.8 |
| $R_f$ of the N-oxide | 0.41 |

EXAMPLE 13

An effervescent tablet prepared according to Example 8 is added to a single-dose bottle of 5 ml of a 0.2% solution in an aqueous-alcoholic mixture (alcohol strength 35°) of 2,4-diamino-6-n-butyloxypyrimidine 3-oxide.

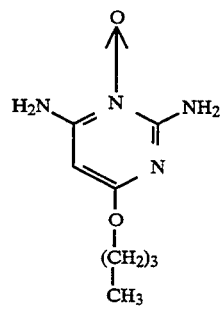

After the effervescence has ceased, a sulpho-conjugated derivative spot is observed in TLC.

EXAMPLE 14

An effervescent tablet prepared according to Example 8 is added to a single-dose bottle of 5 ml of a 0.5% solution in an aqueous-alcoholic mixture (alcohol strength 35°) of 2,4-diamino-6-n-hexylaminopyrimidine 3-oxide.

After the effervescence has ceased, a sulpho-conjugated derivative spot is observed in TLC.

EXAMPLE 15

An effervescent tablet prepared according to Example 8 is added to a single-dose bottle of 5 ml of a 0.5% solution in an aqueous-alcoholic mixture (alcohol strength 35°) of 2,6-diamino-4-piperidinopyridine 1-oxide.

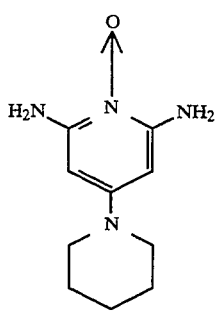

After the effervescence has ceased, a sulpho-conjugated derivative spot is observed in TLC.

We claim:

1. A multicomponent agent or "kit" for preparing a ready-to-use composition of the sulpho-conjugated form of pyridino, pyrimidino or triazino N-oxide compounds in a physiologically acceptable medium, said agent or kit comprising:

a) a component comprising at least one compound of formula (I):

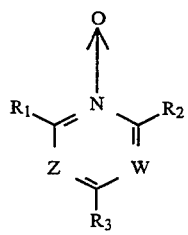

in which:

$R_1$, and $R_2$ denote a $C_1$ to $C_8$ lower alkyl or an amino group;

W and Z each denote a —CH= or —N= group;

$R_3$ denotes a

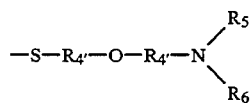

or —H group; and $R_4$ denotes a linear or branched $C_1$ to $C_{18}$ alkyl group which is unsubstituted or substituted by one or more halogen atoms, a $C_1$ to $C_{18}$ alkenyl, $C_3$ to $C_7$ cycloalkyl, aryl or aralkyl group;

$R_5$ and $R_6$ denote, independently of each other, a hydrogen atom or a group such as defined for $R_4$; or $R_5$ and $R_6$ form with the nitrogen to which they are attached, a heterocyclic residue selected from the group consisting of piperidino, pyrrolidinyl, 2-methylpyrrolidinyl, 3-butylpyrrolidinyl, 2-isohexylpyrrolidinyl, 2,3-dimethylpyrrolidinyl, 2,2-dimethylpyrrolidinyl, 2,5-diethylpyrrolidinyl, 3-tert-butylpyrrolidinyl, 2,3,5-trimethylpyrrolidinyl, 3,4-dioctylpyrrolidinyl, 2-methylpiperidino, 3-methylpiperidino, 4-methylpiperidino, 3-isopropylpiperidino, 4-tert-butylpiperidino, 2- methyl-5-ethylpiperidino, 3,5-dipentylpiperidino, 2,4,6-trimethylpiperidino, 2,6-dimethylpiperidino, 2,6-dimethyl-4-octylpiperidino, 2,3,5-trimethylpiperidono, 2-methylheptamethylene-imino, 5-butylheptamethylene-imino, 2,4-diisopropylheptamethylene-imino, 3,3-diethylheptamethylene-imino, 2,5,8-trimethylheptamethylene-imino, 3-methyloctamethylene-imino, 2,9-diethyloctamethylene-imino, 4-isooctyloctamethylene-imino, 4-methylpiperazinyl, 4-isopropylpiperazinyl, groups; or their addition salts with acids; and b) a component comprising at least one sulphating agent;

at least one of said components a) and b) further comprising a physiologically acceptable liquid medium selected from the group consisting of aqueous, aqueous-alcoholic and anhydrous mediums;

wherein, components a) and b) are intended to be brought into contact with one another to prepare the ready-to-use composition.

2. The agent or kit according to claim 1, characterised in that the sulphating agent is selected from the group consisting of polymeric and monomeric $SO_3$-amine complexes.

3. The agent or kit according to claim 1, characterised in that the sulphating agent is selected from the group consisting of the $SO_3$ and tertiary amine complexes.

4. The agent or kit according to claim 1, characterised in that the sulphating agent is selected from the group consisting of the $SO_3$-trimethylamine and $SO_3$-triethylamine complexes.

5. The agent or kit according to claim 1, characterised in that the component a) includes said physiologically acceptable liquid medium, the component b) is in solid form, and the component b) is soluble in the component a).

6. The agent or kit according to claim 1, characterised in that the component a) comprises 0.1 to 10% by weight of the compound of formula (I) relative to the total weight of components a) and b).

7. The agent or kit according to claim 1, characterised in that the pH of the ready-to-use composition produced by bringing into contact components a) and b) is between 5 and 9.

8. The agent or kit according to claim 1, characterised in that the molar concentration of sulphating agent present in component b) is between 1 and 100 times the molar concentration of the compound of the formula (I) present in component a).

9. The agent or kit according to claim 1 characterised in that component a) is in the form of an aqueous, aqueous-alcoholic or anhydrous solution of a compound of formula (I); and component b) is in solid form comprising the sulphating agent.

10. The agent or kit according to claim 9, characterised in that the component (b) is in the form of an effervescent tablet comprising the sulphating agent and a carbon dioxide gas generating system consisting of a water soluble solid acid and a carbonate.

11. The agent or kit according to claim 1, characterised in that the compound of formula (I) is selected from the group consisting of minoxidil, 2,4-diamino-6-piperidinotriazine 3-oxide, 2-amino-4-methyl-6-piperidinopyrimidine 3-oxide, 2-methyl-4-amino-6-piperidinopyrimidine 3-oxide, 2,4-dimethyl-6-piperidinopyrimidine 3-oxide, 2,4-diamino-6-n-butyloxypyrimidine3-oxide, 2,4-diamino-6-(n-hexylamino)-pyrimidine 3-oxide and 2,6-diamino-4-piperidinopyridine 1-oxide.

12. Method for using the agent or kit according to claim 1, comprising bringing components a) and b) into contact with one another and permitting the sulphating agent of component b) to react with the compound of formula (I) of component a), thereby producing the ready-to-use composition.

13. Method for preparing a ready-to-use sulpho-conjugated form of pyridino, pyrimidino or triazino N-oxide compounds in a physiologically acceptable medium, comprising the steps of:

providing a first stored component (a) which comprises at least one compound of formula (I):

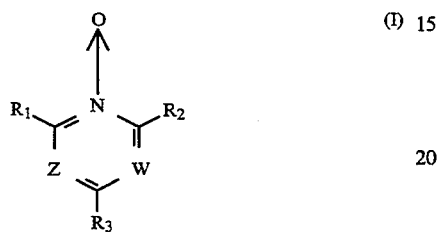

in which:

$R_1$ and $R_2$ denote a $C_1$ to $C_8$ lower alkyl or an amino group;

W and Z each denote a —CH= or —N= group;

$R_3$ denotes a

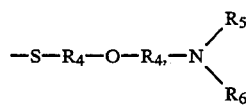

or —H group; and $R_4$ denotes a linear or branched $C_1$ to $C_{18}$ alkyl group which is unsubstituted or substituted by one or more halogen atoms, a $C_1$ to $C_{18}$ alkenyl, $C_3$ to $C_7$ cycloalkyl, aryl or aralkyl group;

$R_5$ and $R_6$ denote, independently of each other, a hydrogen atom or a group such as defined for $R_4$; or $R_5$ and $R_6$ form with the nitrogen to which they are attached, a heterocyclic residue chosen from the group consisting of piperidino, pyrrolidinyl, 2-methylpyrrolidinyl, 3-butylpyrrolidinyl 2-isohexylpyrrolidinyl, 2,3-dimethylpyrrolidinyl, 2,2-dimethylpyrrolidinyl, 2,5-diethylpyrrolidinyl, 3-tert-butylpyrrolidinyl, 2,3,5-trimethylpyrrolidinyl, 3,4-dioctylpyrrolidinyl, 2-methylpiperidino, 3-methylpiperidino, 4-methylpiperidino, 3-isopropylpiperidino, 4-tert-butylpiperidino, 2-methyl-5-ethylpiperidino, 3,5-dipentylpiperidino, 2,4,6-trimethylpiperidino, 2,6-dipentylpiperidino, 2,6-dimethyl-4-octylpiperidino, 2,3,5-trimethylpiperidino, 2-methylheptamethylene-imino, 5-butylheptamethylene-imino, 2,4-diisopropylheptamethylene-imino, 3,3-diethylheptamethylene-imino, 2,5,8-trimethylheptamethylene-imino, 3-methyloctamethylene-imino, 2,9-diethyloctamethylene-imino, 4-isooctyloctamethylene-imino, 4-methylpiperazinyl, 4-isopropylpiperazinyl groups; or their addition salts with acids;

providing a second stored component (b) which comprises at least one sulphating agent; and then mixing the stored components (a) and (b);

wherein at least one of said first component (a) and said second component (b) comprises a physiologically acceptable liquid medium selected from the group consisting of aqueous, aqueous-alcoholic and anhydrous mediums.

* * * * *